United States Patent
Goldstein et al.

(10) Patent No.: US 8,437,492 B2
(45) Date of Patent: May 7, 2013

(54) EARPIECE AND METHOD FOR FORMING AN EARPIECE

(75) Inventors: Steven Goldstein, Delray Beach, FL (US); John Patrick Keady, Fairfax Station, VA (US); Paul Calvert, Assonet, MA (US)

(73) Assignee: Personics Holdings, Inc., Boca Raton, FL (US)

( * ) Notice: Subject to any disclaimer, the term of this patent is extended or adjusted under 35 U.S.C. 154(b) by 179 days.

(21) Appl. No.: 13/051,418

(22) Filed: Mar. 18, 2011

(65) Prior Publication Data

US 2011/0228963 A1   Sep. 22, 2011

Related U.S. Application Data

(60) Provisional application No. 61/315,393, filed on Mar. 18, 2010.

(51) Int. Cl.
*H04R 25/00* (2006.01)

(52) U.S. Cl.
USPC ............ 381/380; 381/326; 381/328

(58) Field of Classification Search ............... 381/23.1, 381/380, 322–328; 181/129, 130, 135, 136; 264/279
See application file for complete search history.

(56) References Cited

U.S. PATENT DOCUMENTS

| | | |
|---|---|---|
| 6,137,889 A | 10/2000 | Shennib |
| 6,940,989 B1 | 9/2005 | Shennib |
| 6,984,902 B1 | 1/2006 | Huang |
| 7,161,254 B1 | 1/2007 | Janky |
| 7,453,163 B2 | 11/2008 | Roberts |
| 7,514,804 B2 | 4/2009 | Wang |
| 2009/0022353 A1* | 1/2009 | Goldstein et al. ............ 381/380 |
| 2009/0154747 A1* | 6/2009 | Vestergaard et al. ......... 381/325 |
| 2009/0226017 A1* | 9/2009 | Abolfathi et al. ............ 381/326 |
| 2009/0262966 A1* | 10/2009 | Vestergaard et al. ......... 381/322 |

* cited by examiner

*Primary Examiner* — Tuan D Nguyen
(74) *Attorney, Agent, or Firm* — RatnerPrestia

(57) ABSTRACT

An earpiece is provided containing a thermal activator layer comprised of a first polymer, the thermal activator layer being separated from the tympanic membrane of the user's ear by an air gap, and an acoustical reflector layer, containing a second polymer and pigment particles, adjacent to the thermal activator layer. The earpiece may be produced by sequential introduction of various liquefied components in layers within the ear canal, with the components being cured to provide the thermal activator layer and the acoustical reflector layer.

11 Claims, 2 Drawing Sheets

EARPIECE AND METHOD FOR FORMING AN EARPIECE

CROSS-REFERENCE TO RELATED APPLICATIONS

This application claims priority from U.S. provisional application 61/315,393, filed Mar. 18, 2010, incorporated herein by reference in its entirety for all purposes.

FIELD OF THE INVENTION

The present invention relates to earpieces capable of modifying audio information provided into a user's ear and more particularly, though not exclusively, to earpieces capable of controlling ambient sound to a user's tympanic membrane.

BACKGROUND

Attenuation, or insertion loss in decibels, is the metric by which all hearing protection is judged by consumers and labeled as required by United States Environmental Protection Agency law. The standard solution to provide such protection has been physically occluding the ear canal with either a compressible, oversized earplug, typically constructed of expandable foam, silicone, putty/resins, or fibers. Thus a bias in the metrics of hearing protection performance to date has, always been attenuation; however, this is a very narrow viewpoint which completely ignores often-important interface issues for the users. For example, a user's situation awareness and ability to localize sound stimuli is compromised. Comfort is often gained at the expense of attenuation. The occlusion effect causes unnatural sounding feedback of the user's own voice, making it difficult to modulate the voice output resulting in objections to using the protector and increasing the difficulty of achieving effective in-canal voice pickup for radio communications.

To further elaborate, current technology designed to provide both hearing protection and communications is based on the principle of occluding the outer ear in order to shelter it from the ambient environment. Most common is an earplug of some type which is inserted in the open ear canal, expanding along the radial surfaces of the canal as necessary until a physical seal is established. Furthermore, hearing protection devices, also known as HPDs, are only valuable when properly selected and fit to the user, and worn properly, to counteract imminent acoustical hazards, which unfortunately is often too late. Earplugs, by their very nature, introduce their own set of problems. They are frequently uncomfortable to wear, with the user being very aware of their presence. Additionally, due to significant differences between individuals with respect to the size and shape of their ear canals, it is difficult to provide a single earplug device that fits all users comfortably and effectively. As a result, many currently available earplugs suffer from the following problems, among others:

- Production of the occlusion effect
- Impaired localization
- Compromised speech understanding
- Severely degrades the user's situation awareness
- Often ineffective protection due to improper sizing and insertion
- Uncomfortable and unnatural feeling
- Harbor and introduce bacteria and promote fungal infection
- Challenges in compliance, that is, convincing the user to wear a HPD they "might" need
- User's speech is too loud or too low
- User's lack of confidence in actual protection provided and impaired situation awareness
- Occlusion effect provides its own unnatural 15 dB of amplification of the user's voice in the ear canal
- Impaction of cerumen, that is, earwax
- Not compatible and interoperable with a user's (e.g., a soldier's) current ensemble and communications equipment.

Thus, there remains a need to develop improved earplug devices which avoid or minimize the above-mentioned issues. In particular, it would be highly desirable to provide automatic attenuation for the preservation of a user's hearing functionality during and after noise hazards, while simultaneously providing for external signal detection and localization, as well as radio-connected and selectively attenuated ambient pass-through speech communications.

SUMMARY OF THE INVENTION

The present invention provides an earpiece that uniquely effects acquisition of the user's voice devoid of ambient noise, yielding a clean signal, with the speaking voice acquired through in-canal bone transduction. The device is comfortable to wear even over extended periods of time, but the hearing capabilities of the user can be fully maintained.

Instead of inserting a physically dense, oversize object in the ear canal, the present invention involves delivering and infusing, for example, a multi-liquid microdrop deposition suspension or the like into the ear canal utilizing a metered dosing system. Suspensions or other liquefied components are deposited into the canal, wherein they serially deposit into stratified layers. Once such a set of material layers reside in the canal, they can be cured in place, which can, for example, be accomplished by the excitation of a laser (capable of providing, e.g., blue-wavelength light). Thus, a sequence of layers, each with its own acoustical, thermal, and transmissivity characteristics, can be formed into an elastomeric multilayer collar.

The polymeric collar provides for a snug and thus ideal acoustical seal, hugging the auditory meatus slightly anterior of the intersection of the tympanic membrane and bony region. The polymeric collar impedes environmental sounds from stimulating the tympanic membrane, while also serving as an optical transport system for a means to deliver, via fiber-optic based infrared laser, the user's acoustical surroundings, but at safe sound pressure levels. In addition, the optical transport enables a photo optical coupler to acquire the user's own voice for two-way radio communication. The present invention thus involves the translation of acoustical stimuli to optical-thermal and finally mechanical coupling to regenerate pressure pulses which stimulate the tympanic membrane. The invention is capable of providing highly effective protection against noise-induced injuries to the ear, including both those of the common neural manifestation or the less common conductive losses.

In one aspect of the invention, an earpiece within an ear canal of a user is provided which comprises:

a) a thermal activator layer comprised of a first polymer and pigment particles, the thermal activator layer being separated from the tympanic membrane of the user's ear by an air gap; and b) an acoustical reflector layer comprised of a second polymer adjacent to the thermal activator layer.

The thermal activator layer may be selected to be absorptive to electromagnetic radiation having a first wavelength and reflective of electromagnetic radiation having a second wavelength, while the acoustical reflective layer may be selected to be substantially transparent to the first wavelength. The electromagnetic radiation may include, without being limited to, wavelengths within the visible spectrum, the infrared spectrum and the ultraviolet spectrum.

In another aspect of the invention, a method of forming an earpiece is provided which comprises the steps of:
 a) introducing into an ear canal of a user adjacent to the tympanic membrane a first layer which provides a temporary foam layer;
 b) introducing into the ear canal adjacent to the first layer a second layer in liquefied form which comprises one or more polymer precursors and pigment particles capable of being cured to form a thermal activator layer comprised of a first polymer and pigment particles;
 c) introducing into the ear canal adjacent to the second layer a third layer in liquefied form which comprises one or more polymer precursors (typically, without pigment particles) capable of being cured to form an acoustical reflector layer comprised of a second polymer; and
 d) curing the second layer and the third layer, simultaneously or sequentially.

In another embodiment of the invention, an earpiece within an ear canal of a user is provided which comprises:
 a) a thermal activator layer comprised of a first polymer and pigment particles, the thermal activator layer being immediately adjacent to or in at least partial contact with the tympanic membrane of the user's ear; and
 b) an acoustical reflector layer comprised of a second polymer adjacent to the thermal activator layer.

A method of making the above-described earpiece is also provided by the invention, the method comprising the steps of:
 a) introducing into an ear canal adjacent to or in at least partial contact with the tympanic membrane a first layer in liquefied form which comprises one or more polymer precursors and pigment particles capable of being cured to form the thermal activator layer;
 b) introducing into the ear canal adjacent to the first layer a second layer in liquefied form which comprises one or more polymer precursors capable of being cured to form the acoustical reflector layer; and
 c) curing the first layer and the second layer, simultaneously or sequentially.

In the context of the above-described curing step c) or d), "simultaneously or sequentially" means that the individual curable layers may be cured at the same time ("simultaneously") or at different times or in an overlapping manner ("sequentially"). In one embodiment, for example, both layers are cured simultaneously. For example, initiation of curing may occur at the same time (e.g., the different layers are exposed to electromagnetic radiation capable of beginning the curing process at the same time). In another exemplary embodiment, a first layer is cured and thereby converted to the thermal activator layer before a second layer is deposited on the thermal activator layer and cured. In still another embodiment, curing of the first layer is initiated and while the first layer is still in the process of curing the second liquid layer is applied to the first layer and curing of that second layer then also initiated by exposing the second layer to electromagnetic radiation of a suitable wavelength (which may also promote further curing of the first layer).

Further areas of applicability of exemplary embodiments of the present invention will become apparent from the detailed description provided hereinafter. It should be understood that the detailed description and specific examples, while indicating exemplary embodiments of the invention, are intended for purposes of illustration only and are not intended to limit the scope of the invention.

BRIEF DESCRIPTION OF THE DRAWINGS

Exemplary embodiments of the present invention will become more fully understood from the detailed description and the accompanying drawings, wherein.

DETAILED DESCRIPTION OF THE INVENTION

Figure 1:
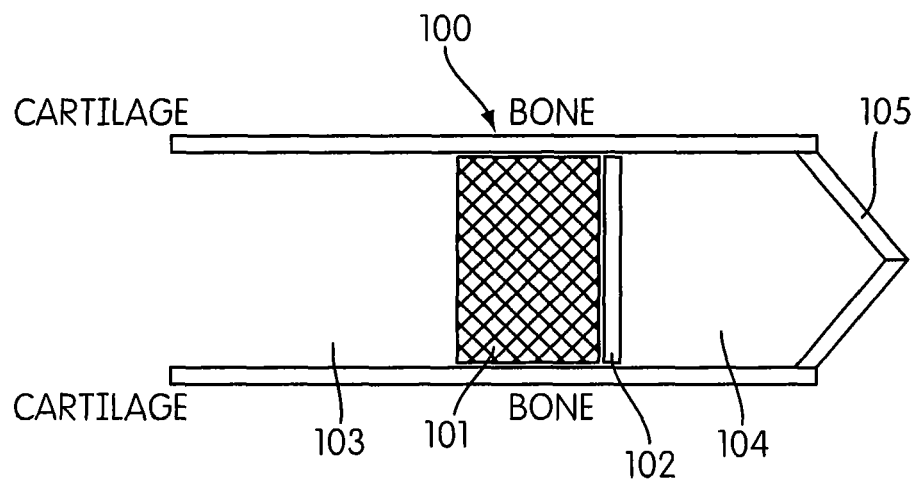
FIG. 1 illustrates at least one exemplary embodiment of an earpiece in accordance with the present invention.

The following description of exemplary embodiment(s) is merely illustrative in nature and is in no way intended to limit the invention, its application, or uses.

Processes, techniques, apparatus, and materials as known by one of ordinary skill in the art may not be discussed in detail but are intended to be part of the enabling description where appropriate.

Notice that similar reference numerals and letters refer to similar items in the following figures, and thus once an item is defined in one figure, it may not be discussed or further defined in the following figures.

In all of the examples illustrated and discussed herein, any specific values, for example the sound pressure level change, should be interpreted to be illustrative only and non-limiting. Thus, other examples of the exemplary embodiments could have different values.

FIG. 1 illustrates at least one exemplary embodiment of the earpiece of the present invention. The earpiece 100 includes multiple layers, including an acoustical reflective layer 101 and a thermal activator layer 102, which is positioned within an ear canal 103 of a user. An air gap 104 is present between the thermal activator layer 102 and the tympanic membrane 105.

Figure 2:
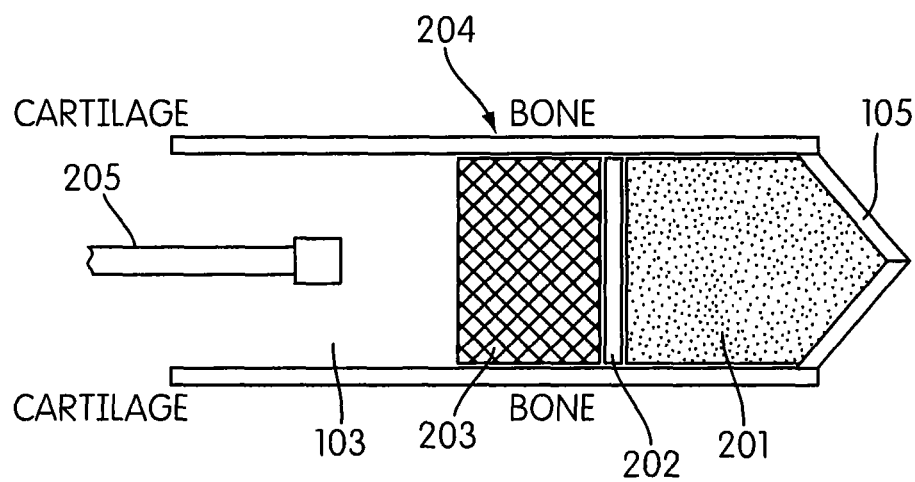
FIG. 2 illustrates at least one exemplary embodiment of the present invention in which a precursor to an earpiece is provided.

FIG. 2 illustrates at least one exemplary embodiment for forming an earpiece in accordance with the present invention. A supporting, temporary foam 201 is introduced first into the ear canal 103 to form a barrier about the tympanic membrane 105. A second layer 202 which comprises one or more polymer precursors and pigment particles is then introduced adjacent to temporary foam 201. Then, a third layer 203 which comprises one or more polymer precursors is introduced adjacent to second layer 202 to form an earpiece precursor 204. A electromagnetic radiation delivery system 205 directs electromagnetic radiation to the earpiece precursor. The electromagnetic radiation supplied by the electromagnetic radiation delivery system can be of any wavelength needed to cure the polymer precursors used to form the acoustical reflector layer and thermal activator layer when inserted. For example, a blue light emitting diode may be utilized, although the use of devices capable of emitting other wavelengths (e.g., ultraviolet light) are also possible. Following curing of second layer 202 (to provide a thermal activator layer) and third layer 203 (to provide an acoustical reflector layer) and collapse or dissipation of temporary foam 201 (to provide an air gap), the earpiece arrangement illustrated in FIG. 1 may be obtained.

Once cured, the thermal activator layer is designed to absorb at least one wavelength of electromagnetic radiation emitted by the electromagnetic radiation delivery system 205, for example, the wavelength may be in the infrared region.

The cured acoustical reflector layer is, in one embodiment, optically transparent, thus allowing for the transmission of energy such that the tympanic membrane can be stimulated with precise control for selective hearing and directional functionality. Although examples of the electromagnetic radiation delivery system 205 are described below with respect to light emitting diodes (LEDs), it is understood that the electromagnetic radiation delivery system 205 may include any source of electromagnetic radiation capable of providing suitable energy from earpiece 100 and to stimulate the tympanic membrane via earpiece 100.

Figure 3:
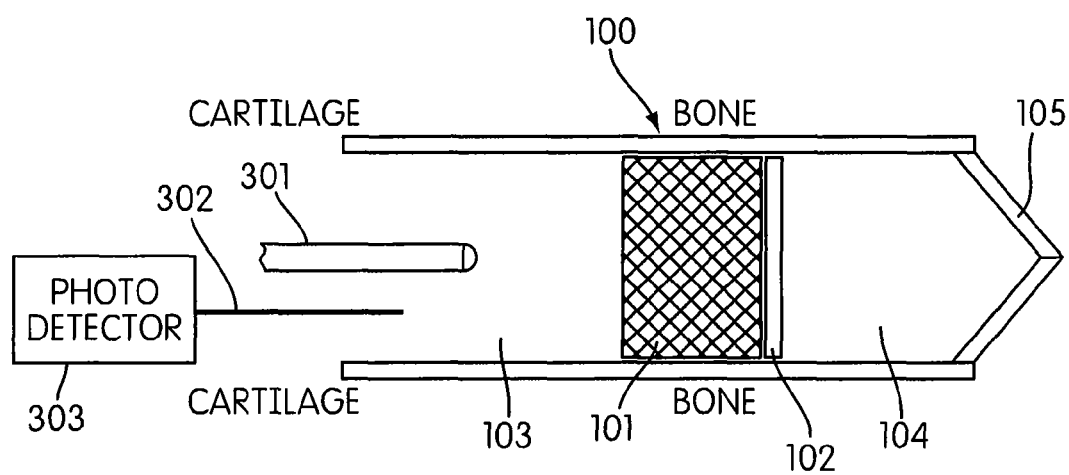
FIG. 3 illustrates at least one exemplary embodiment of the present invention in which an earpiece is used in cooperation with an LED infra-red emitter, a fiber optic cable and a photo detector.

FIG. 3 illustrates an embodiment of the invention wherein the earpiece 100 of FIG. 1 is utilized in cooperation with an LED infra-red (IR) emitter 301 capable of being pulsed at acoustic frequencies and a fiber optic cable 302 which functions to pick up wall vibration from speech. The fiber optic cable 302 may be coupled to a photo detector 303, for example, as part of a voice communication system, described further below.

As previously mentioned, a supporting, temporary foam is inserted first into an ear canal to provide a barrier between the tympanic membrane and the subsequently introduced second layer and third layer. The additional layers are formed on the foam layer which then disintegrates or collapses leaving an air gap between the tympanic membrane and any subsequently applied layers. For example, the supporting, temporary foam can be comprised of a dilute biodegradable biopolymer. The foam can, for example, be a two part mix of alginate and calcium solution (e.g., calcium chloride or the like) or alginate and hyaluronate at very low dilution to form a stable foam. The ingredients can be biodegradable and cytocompatible. A blowing agent can be used (such as citric acid and bicarbonate or a physical blowing agent such as a volatile hydrocarbon or halogenated hydrocarbon) to form bubbles in the foam. The foam could also be created by mechanical agitation (e.g., whipping or frothing) to incorporate gas bubbles into a biopolymer-containing mixture. A single biopolymer can also be used.

The thermal activator layer can be comprised of the same material as the acoustical reflector layer (to be discussed) but with varying amount of pigment to absorb the particular heating electromagnetic radiation (e.g., infrared) used. For example, an infrared laser or the blue laser can be used to heat the thermal activator layer. Varying the laser pulse frequency can result in a varying frequency heating of the thermal activator layer, triggering vibrations that translate into deformations of the tympanic membrane simulating sound. Acoustic signals range from about 20 Hz to about 20 kHz.

The acoustical reflector layer can be comprised of various materials. In one embodiment of the invention, one or more polymer precursors in liquid form may be introduced into the ear canal and then cured to provide a polymer. Such curable polymer precursors may include, by way of example, monomers, oligomers or even polymers capable of being reacted, polymerized, and/or crosslinked. Liquefication may be achieved by placing such precursors in a suitable liquid medium, such as in solution or in suspension (dispersion). The liquid medium, if any, is preferably selected to be non-hazardous; for example, water or an aqueous system can be used. In one embodiment, the polymer precursors are delivered in neat (bulk) liquid form, i.e., without any solvent or non-reactive diluent. The viscosity, flow and/or other characteristics of the liquefied material as introduced are varied or selected as may be desirable to provide a readily dispensable liquid which is capable of forming a liquid layer within the ear canal of the desired thickness and configuration prior to being cured and converted into non-flowable, solid form. Thickeners, flow control agents, rheology control agents and the like may be used for this purpose. Other additives may also be present as desired, including for example, catalysts (initiators), crosslinking agents, diluents, plasticizers, stabilizers, antioxidants, fillers, and the like.

A wide variety of polymer technologies may be utilized in the present invention. For example, the family of biocompatible partly-hydrophilic cross-linked acrylic copolymers used in soft contact lenses, based around hydroxyethylmethacrylate monomer (HEMA), are generally suitable for use. These acrylic copolymers are tunable across a wide range of moduli, water swellability, tissue adhesiveness and other human factor issues, by selecting and adjusting parameters such as (co)monomer composition, molecular weight, crosslinking density, and so forth. Comonomers useful in preparing such acrylic copolymers can include HEMA, hydroxypropylmethacrylate and higher members of the series, the equivalent acrylates, vinylpyrrolidone, various silicone (meth)acrylates, similar diacrylates and dimethacrylates as cross-linkers (e.g., ethyleneglycol di(meth)acrylate and other glycol di(meth) acrylates), polyethyleneglycol acrylates, polyethyleneglycol diacrylates, polyethyleneglycol methacrylates and polyethyleneglycol dimethacrylates, a range of urethane diacrylates and dimethacrylates and many others used in optical or dental applications and their relatives.

The chosen polymer precursors (e.g., monomers) can be cured by blue light using an eosin catalyst, or any other suitable catalyst (which may be selected based upon the polymer precursors and curing light wavelength used), for example as used by Genzyme and is known to be cytocompatable, with an exemplary curing time of about 1 minute.

The polymeric collar formed by the thermal activator layer and the acoustical reflector layer in one embodiment provides a complete seal across the diameter of the ear canal. That is, one or both of these layers span completely across the ear canal, such that no gaps exist. In one embodiment, one or both of the layers are continuous, having no openings, holes or perforations, and are substantially uniform in thickness and largely normal to the ear canal axis.

Once its use is no longer needed, the earpiece can be removed from the ear canal via force or via enzymes. Thus, in such an exemplary embodiment, monomers can be included in the polymer precursors used to form the absorptive (thermal activator) and acoustical reflective layers that contain groups vulnerable to enzyme attack. The earpiece can thus be cleaved by contacting the earpiece with the enzyme during a removal step wherein the enzyme will break up the polymers into smaller soluble units that can be washed out. Several enzymatic systems can be used. For example, one can incorporate phosphate diesters into the polymer and cleave these with alkaline phosphatase (a hydrolase enzyme capable of cleaving phosphate linkages). An alternative method is to incorporate monomers (e.g., acrylate monomers) containing sugar linkages and to cleave these with amylases such as those currently used in laundry detergents. Still another approach is to incorporate monomers containing amide linkages and to cleave these with proteolytic enzymes. The enzyme breaks down the earpiece to the level where it is easily removable from the ear canal. Complete disintegration of the earpiece may not be necessary (i.e., it may be sufficient to degrade just a portion of the outer surface of the polymeric collar such that the snug seal against the ear canal is broken).

The acoustical reflector layer may be selected to provide acoustic attenuation by reflection due to impedance mismatch at the air/polymer interface. In one embodiment, the polymer of the thermal activator layer and/or the acoustical reflector layer is soft to match the elastic properties of tissue. In another embodiment, the polymer(s) continually expands after cure to ensure good seal to tissue. In still another embodiment, the polymer(s) is enzymatically degradable for removal after use. One particularly suitable material for use in the invention is a soft hydrophilic acrylate photocured by a blue-light eosin catalyst and containing biodegradable links in the polymer chain.

The thermal activator layer may conveniently be comprised of the same polymeric material as the acoustical reflector layer, but in another embodiment is comprised of a different polymeric material. The thermal activator layer differs from the acoustical reflector in being pigmented with a pigment. Any pigment capable of absorbing electromagnetic radiation energy from a source such as an infrared or blue light laser and converting the electromagnetic radiation energy into heat may be employed. Typically, the pigment will be in finely divided, particulate form. Suitable pigments include, for example, carbon black, metallic oxides, metal powders, and the like; mixtures of different pigments may be utilized. The particle size and amount of pigment in the thermal activator layer may be varied as desired to impart particular characteristics and properties to such layer. The thermal activator layer may, for example, be about 0.05 to about 1.5 (e.g., about 0.1) mm in thickness and capable of absorbing incoming laser light, thereby producing local heat and expanding gas adjacent to the tympanum via the photoacoustic effect.

The air space adjacent to the tympanum is initially defined by a temporary foam supporting the soft polymer layers (the acoustical reflector layer and the thermal activator layer). The temporary foam in effect acts as a template or support for the subsequently applied polymer layers, but then dissipates, collapses or is absorbed or degraded once those polymer layers have been created and become self-supporting.

Attenuation of external sound mainly occurs by reflection at the soft polymer/air interface in the ear canal. For a typical soft polymer useful in the present invention, the attenuation is estimated to be >25 dB at 1 kHz from impedance mismatch. Additional high frequency attenuation may be achieved due to surface skin, while additional low frequency attenuation due to damping in the polymer may also occur.

In one embodiment of the invention, internal sound is produced by heating of the thermal activator layer by 0.2 milliKelvin, producing a gas pressure wave equivalent to 80 dB. At 1 kHz the required energy input is 1 mWatt.

One potential advantage of the present invention is that heating of the ear canal can be minimized. Heat transfer calculations show that 10 mW of input energy can be readily absorbed and converted to a temperature rise of 1.5 K in the thermal activator layer. Slow buildup of heat in the ear should not be a problem.

The materials employed to provide the first injectable layer (temporary foam), second injectable layer (which when cured will form the thermal activator layer), and third injectable layer (which when cured will form the acoustical reflector layer) may be introduced into the ear canal of a subject by any suitable method or apparatus. For example, an insertion device may be used which is a microdrop system capable of dispensing three fluids sequentially onto the tympanum. The approximately millimeter sized droplets can be expelled from a soft tube at about 1 m/s from a distance of about 5 mm from the tympanum. The drops will spread to form a multi-layer film: the first layer is a temporary water-based foam, the second layer is the precursor to the thermal activator layer (typically containing monomer or other polymer precursor plus carbon or other pigment particles), and the third layer is the precursor to the acoustical reflector layer (typically containing monomer or other polymer precursor, but few or no pigment particles). Following delivery, the films will be exposed to light from a blue diode laser (or other light electromagnetic radiation sources of appropriate, effective wavelength) to cure the polymer precursor(s) present in the second and third layers, thereby converting them into polymeric form. This curing may be performed simultaneously or sequentially. In one advantageous embodiment, for example, the second layer is cured before introduction and formation of the third layer. Converting the second layer to polymeric form before the third layer is applied will help to avoid the mixing of the constituents of the different layers which may otherwise occur if both layers are applied and maintained in liquid film form before any curing is carried out.

Subsequent to use, the device can be removed using any suitable method. For example, a dispenser may be used to dispense an enzyme solution containing one or more enzymes such as an esterase that will break down the device over a period of, for example, an hour and allow it to be flushed from the ear. This dispenser can be the same device used to insert the liquid components used to form the earpiece.

An embodiment of the delivery and curing system that can be used in conjunction with the present invention may be further described as follows. The dispenser may be a low-voltage battery-operated portable dispensing "engine" capable of delivering on-demand a plurality of liquefied components (e.g., suspensions, solutions or bulk admixtures) providing light-curable (e.g., visible light-curable) polymer precursors (monomers, oligomers, etc.). These differentiable components, upon curing into distinct, stratified polymeric layers within the canal, act as both an acoustic barrier and photoacoustic transducer by which the laser energy is propagated and collected. The dispenser may be selected and designed to have one or more of the following features:

Small enough for a short pocket
    Consumable, thus affordable
    Rugged, waterproof
    Accurate user canal sizing through metered dispensing The liquefied components may be selected to provide one or more of the following features:

Non-toxic
    Acoustical advantages provided by composite structural layering

The earpiece of the present invention may be utilized in conjunction with a communication device such as a wearable ultra low-wattage laser and photo detection system, and associated acoustical transducers. The communication device may be selected and designed to have the following features:

Unimpaired localization
    No occlusion effect
    No maintenance
    Compatible with existing radios for incoming transmitted speech
    Preserves and enhances ambient speech communication capability
    Enables/enhances acoustic detection, identification
    Attenuates hazardous noise to safe levels
    Effective for impulsive as well as continuous noise
    Fishing line-size fiber optic cable inserted in ear entrance which sends and receives acoustical signals.
    Power consumption (Laser <10 mW)–Total power consumption 30 mA/3 volts
    Environmental ruggedness
    Customized fit for the individual; Consistent, reliable, and comfortable fit.

Secure and stable in the ear; high-integrity seal is resistant to linear g-forces and angular accelerations of the head which cause other HPDs to dislodge.

L/R earphones communicate with each other in order to maximize localization performance Reduction of signal pass-through latency due to optical transmission No tissue pressure-necrosis since no contact with radially expandable foam.

The earpiece, dispenser, and communication device together yield the following mechanisms: 1) an in situ construction in a user's ear of an optically-driven photoacoustic transducer which is enzymatically degradable when no longer required, 2) an acoustic mirror which reflects airborne sound waves for mitigation of hazardous or interfering environmental or ordnance noise, 3) an auditory meatus optical vibration sensor for voice communication. The following advantages may thereby be realized using the invention:

Noise protection is passive and always on
No need for manual controls to be operated by the wearer
Instantaneous pass-through of voice and signals
Comfortable over long periods
Always worn (on) and ready for protection By using a fiber-optic based laser to both stimulate the tympanic membrane as well as acquire the minute oscillations of auditory meatus activated during speaking, the system utilizing the earpiece of the present invention is not only robust, but also immune to RF issues while offering great human factors benefit. While the ca. 2 mm thick low-durometer polymeric collar elegantly resides in the ear canal and is coupled to the fiber-optic interface, a variety of possible locations for remotely mounting the infrared laser, photo detector, associated electronics and power supply can be utilized depending upon application needs, without losing transmission efficiency. Possible mounting locations include: helmet, goggles, eyeglass temples or behind the ear. All of these should prove practical for the user, e.g., a dismounted soldier.

An exemplary illustrative embodiment of a delivery and curing system which can be employed in connection with the present invention is as follows. Four liquefied components (containing, for example, a foam-generating composition, polymer or polymer precursor compounds, or an enzyme solution) are stored in a 4-ounce portable dispensing container. Each liquefied component is injected into the ear canal via a short low durometer silicone tube, which is attached to a battery operated microactuator drive. The system is designed to allow the user to vary the desired amount of passive attenuation, which is accomplished by adjusting a simple dial on the face of the container. The silicone tube is equipped with a soft polymer stop flange, preventing accidental over-insertion into the canal.

The four fluids, each about 4 ml in volume, are stored in four separate reservoirs similar to 4 ml syringe barrels. A low voltage, battery-operated, microactuator drives droplets of the appropriate liquid down a short length of soft microbore tubing and ejects a metered series of drops towards the tympanic membrane at about 0.1 meter/second in a sequential manner.

The first fluid forms a layer (a base layer) of temporary aqueous foam to space the next layers away from the tympanic membrane. Once it covers the membrane, it provides for temporary scaffolding for depositing the next layer to be built upon. Typically, the temporary foam is approximately 1 to 3 mm (e.g., about 2 mm) deep, thereby providing for an air gap of similar dimensions once the foam has collapsed or dissipated. The thermal activator layer thus will correspondingly be spaced about 1 to about 3 mm from the tympanic membrane, typically, once the earpiece has been fully formed within the ear canal. However, in other embodiments the thermal activator layer may be positioned closer to the tympanic membrane, i.e., less than 1 mm, e.g., 0.1 to 1 mm, from the tympanic membrane. The volume of temporary foam introduced into the ear canal may be advantageously controlled as might be desired to provide a desired spacing of the thermal activator layer and the tympanic membrane. In one embodiment of the invention, the temporary foam is omitted altogether, such that the thermal activator layer is positioned immediately adjacent to, or even in at least partial contact with, the tympanic membrane.

The second and third fluids, which are used to provide the thermal activator layer and acoustical reflector layer respectively, may be comprised of biocompatible photocurable polymer precursor (e.g., monomer) mixtures that form, when cured, a soft hydrophilic elastomer bilayer collar. Curing starts within a short time (e.g., ca. 15 seconds), driven by, for example, blue light from a fiber optic attached to the dispensing container. The biocompatible curing system may be based on an eosin photocatalyst, although other such substances known in the art to be capable of catalyzing the electromagnetic radiation-induced curing of the polymer precursors may also be employed. The very short curing cycle provides for a minimum of inconvenience for the user to hold their jaw in a stable position. Now that the polymer precursor or polymer precursors have been activated, it or they may continue to cure to form a polymer matrix for an additional time period (e.g., about one minute) without the need of the light source.

In one embodiment of the invention, after all liquids have successfully been dispensed into the canal, the curing process automatically becomes enabled. In another embodiment, a first liquid is dispensed and then curing of that first liquid is at least initiated before dispensing a second liquid and initiating curing of that second liquid. Within 15 seconds, for example, each exposure (activation) step may be completed. The dispenser may be configured to generate a vibration in the dispensing container and/or to activate an indicating light signifying that the delivery system may be removed, when the desired dispensing and/or curing initiation steps have been completed. The dispensing container may contain sufficient fluids, for example, for about 30 collar installations.

After the earpiece device has served for the period of intended use, the dispensing container may be reinserted into the canal to deliver the fourth liquid, an enzyme system that breaks up the polymeric collar (which may be in the form of a gel) in a desirably short period of time (e.g., 5 minutes) and allows the ear canal to be irrigated to facilitate the complete removal of any remnants of the device.

Functionally, once the polymeric collar is cured, it transforms in one embodiment of the invention to the durometer of a soft-gel encapsulation found in many oral drugs, e.g., a Shore A hardness of from about 10 to about 30. The collar behaves as a highly absorbent acoustical surface. Accordingly, the user experiences up to a 45 dB loss of air conduction, establishing a high level of sound attenuation. In fact, should that maximum level of passive attenuation be required, the user would no longer receive stimulation of the tympanic membrane via air conduction. The amount of passive attenuation may be "dialed-in" during the delivery of the polymer precursor(s) into the canal. Regulating the thickness of the acoustical reflector layer will either increase or decrease the passive noise reduction rating. Typically, the acoustical reflector layer may be about 1 to about 3 mm (e.g., about 2 mm) thick.

Now that the tympanic membrane has been acoustically-isolated from both impulse noises and continuous noises, the user may be simultaneously provided with a means to experience acoustical transparency including situation awareness, localization sensitivity, and full two-way radio communications. To achieve this, an omni-directional ambient acoustical microphone on the distal end of a short length low-modulus polymer-based whip residing in the interior of the non-occluded section of the ear canal may be provided. As the whip is small in diameter (e.g., about 2.5 mm) and terminates superior to the first bend, it allows for the critical pinna and canal cues to be fully acquired with high accuracy. Thus, during playback, the system will properly reproduce precise localization cue details. Such microphones are very robust and are high in signal noise ratio (SNR) characteristics. They allow the user to experience their ambient environment faithfully.

In addition, the microphone and associated electronics may be designed to operate in a 160 dB environment typical of some extreme military impulsive applications, yet attenuate the ambient SPL delivered to the tympanic membrane down to a more conservative level of 115 dB during impulses, and much lower during continuous noises. The operational levels of delivered SPL to the tympanic membrane may range from 10 dB to 100 dB not withstanding flanking pathways. This user adjustable maximum SPL is preserved to ensure the wearer will adequately respond to the acoustical startle reflex when stimulated.

The technique for communicating ambient acoustical stimulus information to the brain, while at the same time protecting the user's hearing, may be accomplished using an acousto-optic converter which processes these acoustical signals into a beam of infrared laser energy. The laser transmits through the acoustical reflector layer and is absorbed and converted to heat at the thermal activator layer, by the pigmented polymer. Heat is then transmitted to the adjacent gas producing miniature gas pressure pulses, thus stimulating the tympanic membrane.

In the case where the polymeric collar is immediately adjacent to or in at least partial contact with the tympanic membrane, the tympanic membrane is mechanically induced (acoustically transferred) via a sealed cavity formed by the polymeric collar, where the vibration of a posterior surface of the polymer collar results in controlled vibration of the tympanic membrane, stimulating the ossicular chain. The thermal activator layer is designed to absorb the communication laser frequency converting the input energy to phonons and thus heat. Typically, it has a thickness of about 50 to about 200 (e.g., about 100) microns. As the laser pulse frequency and intensity varies, the thermal activator layer temperature changes thus expanding and contracting, resulting in acoustic vibrations. The acoustic vibrations result in oscillations of the sealed cavity thus stimulating movement of the tympanic membrane up to 0.1 microns or 100 dB, communicating acoustic information to the user.

As such, the ambient acoustical signals cause deflection of the tympanic membrane, which causes sound to be experienced. When the world is quiet, no gas is excited, thus no pressure is exerted on the tympanic membrane. When the ambient world is reaching "everyday" SPL levels, the varying pressures on the tympanic membrane directly relate to the formation of pressure pulses produced as function of the power output of the laser. When the ambient acoustical world is simply deafening, then the system limits the excitation produced, which in turn controls the SPL perceived at the basilar membrane.

Outbound voice communications using the earpiece device of the present invention may be provided as follows. As the infrared laser passes through the acoustical reflector layer, a portion of the scattered energy is reflected off the anterior portion of the polymeric collar. This scattered energy may be collected and optically coupled to a photo detector. A comparator circuit evaluates the ambient sound against the sound reflected off the walls of the collar, differentiating the two. After a phase shift from latency is accounted for, theoretically, it is expected that the two signals will offset each other and the difference signal acquired from the photo detector is induced by the vibrating walls of the bony region of the canal.

The bony region conveys acoustical stimuli produced either by one's own voice or which vibrates the skull, tissue and bones of the user. As such, a novel means has been created to acquire the user's own voice regardless of the ambient acoustical environment and without the boominess that accompanies in-canal bone conduction microphone technology. The recipient (that is, the other party receiving the call) of the photo detection canal pickup experiences voice communications intelligibility that is on the same level as if the users were speaking from a quiet room. Thus, in a battlefield environment, two-way communications may be conducted with little effort. The user can thereby experience minimal TTS, having full appreciation of all localization cues and retaining good confidence as to situation awareness.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures and functions of the relevant exemplary embodiments.

Although specific numbers may be quoted in the claims, it is intended that a number close to the one stated is also within the intended scope, i.e. any stated number should be interpreted to be "about" the value of the stated number.

Thus, the description of the invention is merely exemplary in nature and, thus, variations that do not depart from the gist of the invention are intended to be within the scope of the exemplary embodiments of the present invention. Such variations are not to be regarded as a departure from the spirit and scope of the present invention.

What is claimed is:

1. An earpiece within an ear canal of a user comprising:
    a) a thermal activator layer comprised of a first polymer and pigment particles, the thermal activator layer being separated from the tympanic membrane of the user's ear by an air gap; and
    b) an acoustical reflector layer comprised of a second polymer adjacent to the thermal activator layer.

2. The earpiece of claim 1, wherein the thermal activator layer is selected to be absorptive to electromagnetic radiation having a first wavelength and reflective of electromagnetic radiation having a second wavelength.

3. The earpiece of claim 2, wherein the acoustical reflective layer is substantially transparent to the first wavelength.

4. The earpiece of claim 1, wherein the thermal activator layer and acoustical reflective layer cooperate to provide a polymeric collar which seals the ear canal.

5. The earpiece of claim 4, wherein the polymeric collar is soft and elastomeric.

6. The earpiece of claim 1, wherein at least one of either the first polymer or the second polymer is a biocompatible partly-hydrophilic cross-linked acrylic copolymer.

7. The earpiece of claim 6, wherein the acrylic copolymer includes hydroxyethylmethacrylate.

8. The earpiece of claim 1, wherein the pigment particles include carbon black particles.

9. A system comprising the earpiece of claim 1 and a communication device.

10. An earpiece within an ear canal of a user comprising:
   a) a thermal activator layer comprised of a first polymer and pigment particles, the thermal activator layer being immediately adjacent to or in at least partial contact with the tympanic membrane of the user's ear; and
   b) an acoustical reflector layer comprised of a second polymer adjacent to the thermal activator layer.

11. A method of making the earpiece of claim 10, comprising the steps of:
   a) introducing into an ear canal adjacent to or in at least partial contact with the tympanic membrane a first layer in liquefied form which comprises one or more polymer precursors and pigment particles capable of being cured to form the thermal activator layer;
   b) introducing into the ear canal adjacent to the first layer a second layer in liquefied form which comprises one or more polymer precursors capable of being cured to form the acoustical reflector layer; and
   c) curing the first layer and the second layer, simultaneously or sequentially.

\* \* \* \* \*